(12) United States Patent
Girard et al.

(10) Patent No.: US 8,598,221 B2
(45) Date of Patent: Dec. 3, 2013

(54) SYNERGISTIC COMBINATION OF ANALGESIC COMPOUNDS

(75) Inventors: Philippe Girard, Margny-les-Compiegne (FR); Marie-Emmanuelle Le Guern, Compiegne (FR); Jean-Marie Gillardin, Jonquieres (FR); Bernard Hublot, Compiegne (FR)

(73) Assignee: Biocodex, Gentilly (FR)

( * ) Notice: Subject to any disclaimer, the term of this patent is extended or adjusted under 35 U.S.C. 154(b) by 247 days.

(21) Appl. No.: 12/959,607

(22) Filed: Dec. 3, 2010

(65) Prior Publication Data

US 2011/0136885 A1   Jun. 9, 2011

(30) Foreign Application Priority Data

Dec. 3, 2009 (FR) ...................... 09 58610

(51) Int. Cl.
*A61K 31/395* (2006.01)
*A61K 31/415* (2006.01)
*A61P 25/04* (2006.01)

(52) U.S. Cl.
USPC ............................ 514/406; 514/450; 514/459

(58) Field of Classification Search
USPC ......................................... 514/406, 450, 459
See application file for complete search history.

(56) References Cited

U.S. PATENT DOCUMENTS 6,316,501 B1 * 11/2001 Miyamoto et al. ............ 514/562

OTHER PUBLICATIONS

Wang, "The clinical analgesic efficacy of oral nefopam hydrochloride", Journal Clinical Pharmacology, Jul. 1979, 19(7), pp. 395-402.*

Dembo, "Central nervous system concentrations of cyclooxygenase-2 inhibitors in humans", Anesthesiology, Feb. 2005, 102(2), pp. 409-415.*
Fletcher et al, "A patient-based national survey on postoperative pain management in France reveals significant achievements and persistent challenges" 2008, pp. 441-451, vol. 137, Pain.
Preliminary French Research Report for FR 09 58610.
Moffat A C et al: "Postoperative Nefopam and Diclofenac. Evaluation of Their Morphine-Sparing Effect After Upper Abdominal Surgery" Anaesthesia, Academic Press, London, GB, vol. 45, No. 4, (Jan. 1, 1990), pp. 302-305.
Lasseter K C et al: "Nefopan HC1 Interaction Study With Eight Other Drugs" Journal of International Medical Research, Cambridge Medical Publications Ltd, GB, vol. 4, No. 3, (Jan. 1, 1976-), pp. 195-201.
Benhamou D (Reprint): "Nefopam and Domaines Techniques Combined Analgesics// Nefopam Et, Recherches (IPC) Association D'Analgesiques" Annales Francaises D'Anesthesie Et De Reanimation, Masson, Paris, FR, (Dec. 1, 2002-), pp. 9-14.
Database WPI Week 200950, Thomson Scientific, London,GB; AN 2009-H90449, XP002578588 & CN 101 411 702 A (Unvi Henan) (Apr. 22, 2009-).

* cited by examiner

*Primary Examiner* — Sreeni Padmanabhan
*Assistant Examiner* — Sahar Javanmard
(74) *Attorney, Agent, or Firm* — B. Schulman; Stites & Harbison, PLLC

(57) ABSTRACT

The present invention relates to a pharmaceutical composition comprising as active substances:
at least one compound of the following general formula (I):

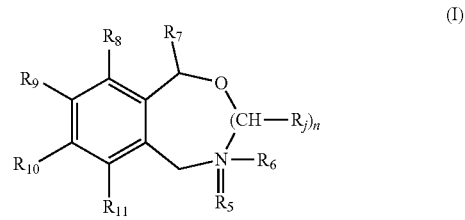

and
at least one inhibitor of type 2 cyclooxygenase (COX-2), notably for use in the prevention or treatment of pain.

9 Claims, 1 Drawing Sheet

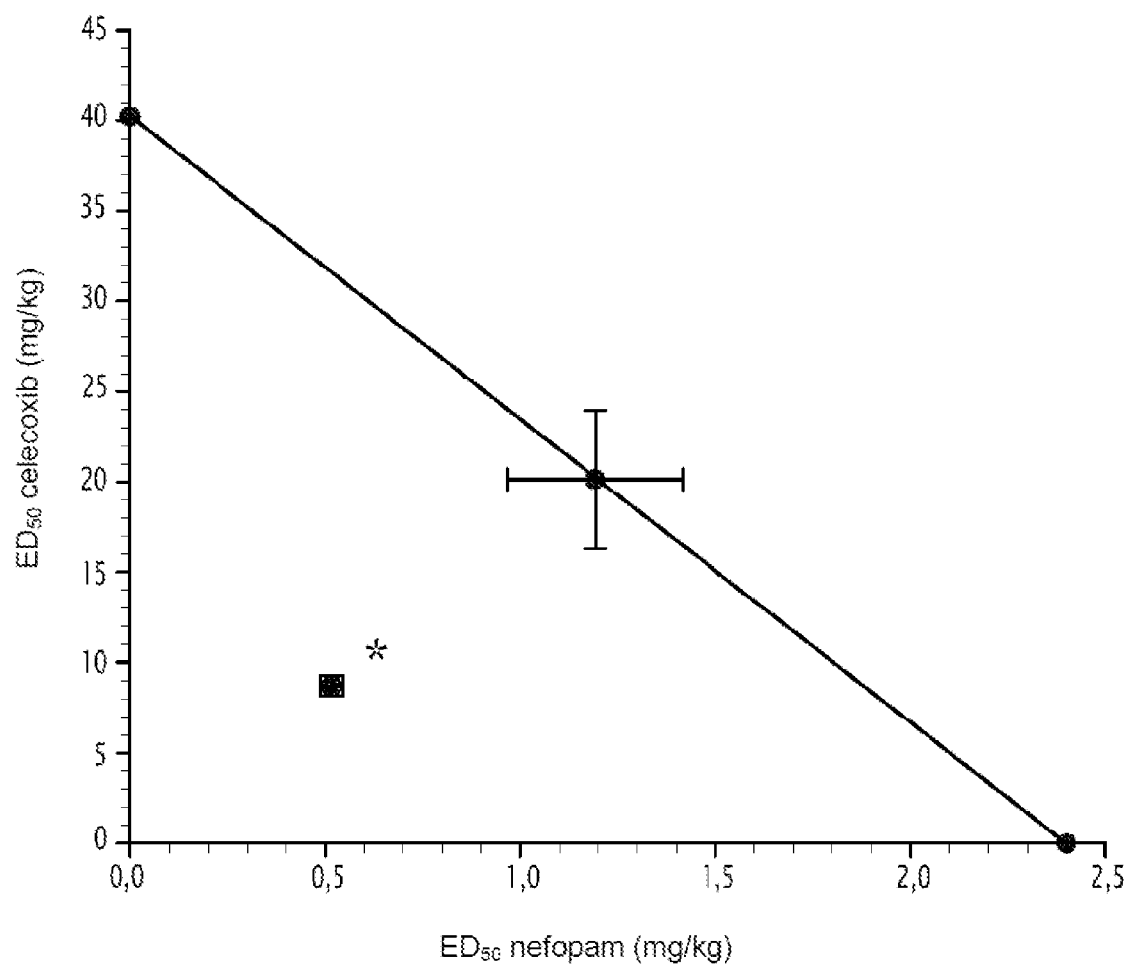

SYNERGISTIC COMBINATION OF ANALGESIC COMPOUNDS

FIELD OF THE INVENTION

The present invention relates to a pharmaceutical composition comprising compounds having synergistic action in the prevention or treatment of pain.

TECHNICAL BACKGROUND

Pharmacologically, the non-steroidal anti-inflammatory drugs (NSAIDs) act by inhibiting an enzyme, cyclooxygenase (COX), and hence the production of prostaglandins that follows from its activity.

COX exists in humans in 2 main isoforms that are involved in different processes. Type 1 cyclooxygenase (COX-1) is notably involved in the physiological process of gastric protection whereas type 2 cyclooxygenase (COX-2) is principally involved in the inflammatory process.

Generally, the conventional, non-selective NSAIDs inhibit both COX-1 and COX-2. In consequence, their use is associated with undesirable side-effects, notably including gastrointestinal lesions, which result directly from inhibition of COX-1.

This has led to the development of selective inhibitors of type 2 cyclooxygenase (COX-2), comprising the drug (or therapeutic) class of the COXIBs, for which the gastrointestinal effects are significantly reduced relative to non-selective NSAIDs (Moore et al. (2006) *BMC Musculoskeletal Disorders* 7:79-91). The main indications of COXIBs are for joint pains. We may mention, as examples, celecoxib (Celebrex®), parecoxib (Dynastat®), valdecoxib (Bextra®), rofecoxib (Vioxx®), etoricoxib (Arcoxia®), or lumiracoxib (Prexige®).

However, one of the main side-effects of the COXIBs is the development of cardiovascular disorders (see for example Caldwell et al. (2006) *J. R. Soc. Med.* 99:132-140). Accordingly, at present, valdecoxib and rofecoxib have been withdrawn from the market and certain countries have refused to grant marketing authorization for parecoxib. Moreover, lumiracoxib has also been refused marketing authorization because of the liver damage that it would cause.

It would therefore be important to be able to benefit from the therapeutic advantages offered by the COXIBs while limiting their side-effects.

Nefopam is the active principle of Acupan®. It is a non-opioid central analgesic in the benzoxazocine class (Klohs et al. (1972) *Arzneimittelforschung* 22:132-3). Its advantages notably include absence of respiratory depressant effects. Its mode of action is still poorly understood but seems to involve inhibition of monoamine reuptake, which distinguishes it from paracetamol and the non-steroidal anti-inflammatory drugs (NSAIDs). At present, nefopam is mainly used for treating postoperative pain. Thus, in France it is administered to about 20% of patients having undergone surgery (Fletcher et al. (2008) *Pain* 137:441-51).

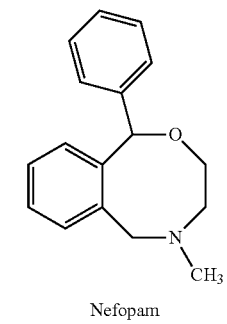

Nefopam

SUMMARY OF THE INVENTION

The present invention arose from the unexpected discovery, by the inventors, of a synergistic analgesic effect between nefopam and celecoxib in an animal model of acute pain.

This synergistic analgesic effect is particularly advantageous in that it makes it possible to benefit from satisfactory analgesia, without foreseeable gastrointestinal involvement, and, owing to the decrease in dose of COXIB to be administered for the same analgesic efficacy, a reduction in cardiovascular risk is anticipated.

Thus, the present invention relates to a pharmaceutical composition comprising, as active substances:

a) at least one compound of the following general formula (I):

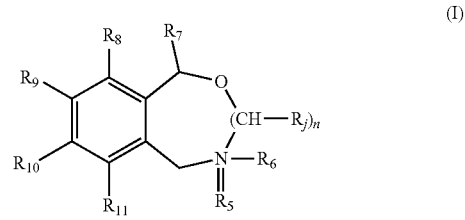

(I)

in which:
- $R_5$ represents O or no group;
- $R_6$ represents H or an alkyl group containing from 1 to 6 carbon atoms;
- n represents an integer from 2 to 4;
- j represents an integer in the range from 1 to n;
- $R_j$, identical or different for each substituted carbon, represents H or an alkyl group containing from 1 to 6 carbon atoms;
- $R_7$ represents a phenyl group optionally substituted with one or more groups, which may be identical or different, selected from the group comprising or consisting of H, an alkyl group containing from 1 to 6 carbon atoms, an alkoxy group containing from 1 to 6 carbon atoms, a trifluoromethyl group, or a halogen atom, in particular I, Br, Cl or F;
- $R_8$, $R_9$, $R_{10}$, $R_{11}$, which may be identical or different, represent H, an alkyl group containing from 1 to 6 carbon atoms, an alkoxy group containing from 1 to 6 carbon atoms, a trifluoromethyl group, or a halogen atom, in particular I, Br, Cl or F;

or a pharmaceutically acceptable salt of this compound; and b) at least one selective inhibitor of type 2 cyclooxygenase (COX-2) or a pharmaceutically acceptable salt of this inhibitor;

optionally together with one or more pharmaceutically acceptable excipients, in particular for inducing analgesia or for use in the prevention or treatment of pain.

The present invention also relates to a compound of general formula (I) as defined above, or a pharmaceutically acceptable salt thereof, in combination with a COX-2-selective inhibitor as defined above, or a pharmaceutically acceptable salt thereof, for use as a medicinal product, in particular for inducing analgesia or for preventing or treating pain.

The present invention also relates to the use of a compound of general formula (I) as defined above, or of a pharmaceutically acceptable salt thereof, in combination with a COX-2-selective inhibitor as defined above, or of a pharmaceutically acceptable salt thereof, for preparing an analgesic medicinal product or one intended for the prevention or treatment of pain.

The present invention also relates to a method for inducing analgesia or for preventing or treating pain in an individual, in which the individual is administered a prophylactically or therapeutically effective amount of at least one compound of general formula (I) as defined above, or of a pharmaceutically acceptable salt thereof, and a prophylactically or therapeutically effective amount of at least one COX-2-selective inhibitor as defined above, or of a pharmaceutically acceptable salt thereof.

The present invention also relates to products containing:
at least one compound of general formula (I) as defined above, or a pharmaceutically acceptable salt thereof, and
at least one COX-2-selective inhibitor as defined above, or a pharmaceutically acceptable salt thereof,
as a combination product for use together or separately for inducing analgesia or for preventing or treating pain.

In a preferred embodiment of the pharmaceutical composition, of the compounds, of the use, of the method and of the products defined above, at least one additional analgesic compound, different from the compounds of general formulae (I) and from the COX-2-selective inhibitor as defined above, or pharmaceutically acceptable salts thereof, is added in combination with the compounds of general formulae (I) and the COX-2-selective inhibitor as defined above.

However, in another preferred embodiment of the pharmaceutical composition, of the compounds, of the use, of the method and of the products defined above, no compound of the following general formula (VI), or pharmaceutically acceptable salt thereof, is included in the pharmaceutical composition or the products, or is in association or in combination with the compounds of general formulae (I) and the COX-2-selective inhibitor as defined above:

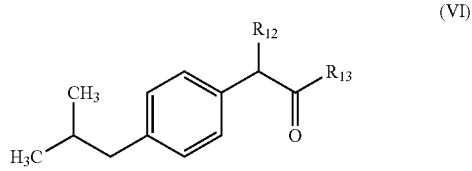

(VI)

$R_{12}$ representing H or an alkyl group containing from 1 to 6 carbon atoms;
$R_{13}$ representing a $OR_{14}$ or $NR_{15}R_{16}$ group;
$R_{14}$ representing H, an alkyl group containing from 1 to 6 carbon atoms, an aryl group containing from 6 to 10 carbon atoms, or an aralkyl or alkaryl group containing from 7 to 20 carbon atoms;
$R_{15}$ and $R_{16}$, which may be identical or different, representing H, OH, an alkyl group containing from 1 to 6 carbon atoms, an aryl group containing from 6 to 10 carbon atoms, or an aralkyl or alkaryl group containing from 7 to 20 carbon atoms.

DESCRIPTION OF FIG. 1

FIG. 1 shows the isobologram of the nefopam-celecoxib combination in the test of cramps induced by acetic acid in the mouse. The star symbol (*) indicates that the representative point of the ED50 of the nefopam-celecoxib combination measured experimentally is located statistically significantly below the straight line of additivity.

DETAILED DESCRIPTION OF THE INVENTION

Prevention or Treatment of Pain

The expression "treating pain" means decreasing or eliminating pain or the sensitivity to said pain. The expression "preventing pain" means that the compounds of general formulae (I) and the COX-2-selective inhibitor as defined above, or pharmaceutically acceptable salts thereof, are administered to an individual before said individual perceives the pain to be treated.

The expression "inducing analgesia" means both decreasing or eliminating pain as well as the sensitivity to said pain. This expression is considered to be equivalent to "use as an analgesic".

The invention relates to the prevention or treatment of any pain whatever its origin.

Preferably, however, the pain prevented or treated according to the invention is acute pain. The expression "acute pain" is well known by a person skilled in the art. It contrasts with the notion of "chronic pain". It is generally considered that acute pain is pain that lasts for less than 3 months.

It is also preferred that the pain prevented or treated according to the invention is pain that is included in the usual indications of compounds of formula (I) or of pharmaceutically acceptable salts thereof according to the invention, notably nefopam, or of COX-2-selective inhibitors or of pharmaceutically acceptable salts thereof according to the invention, notably celecoxib.

Thus, also preferably, the pain prevented or treated according to the invention is acute postoperative pain, rheumatologic pain, pain associated with dysmenorrhoea, and/or pain associated with familial adenomatous polyposis. Particularly preferably, the pain prevented or treated according to the invention is acute postoperative pain and/or rheumatologic pain.

"Acute postoperative pain" denotes pain that results from surgery; in particular, surgery during which an incision is made, healing of which creates pain of the inflammatory type with possible hyperalgesic involvement, for an average duration of 5 to 7 days (Chauvin and Clergue (1998) *Ann. Fr. Anesth. Réanim.* 17:444).

"Rheumatologic pain" according to the invention is preferably pain associated with arthrosis, with osteoporosis, with arthritis, notably infectious or inflammatory, in particular osteoarthritis, with gout, with fibromyalgia, with inflammatory rheumatism, such as rheumatoid arthritis, notably juvenile, or ankylosing spondylitis.

Preferably, the intensity of the pain prevented or treated according to the invention is at least moderate, more preferably at least severe (also called strong). The concepts of "moderate pain" or of "severe pain" are well known by a person skilled in the art. As an example, it is generally considered that moderate pain corresponds to an index from 4 to 6 and severe pain to an index from 7 to 9 on a numerical pain scale graduated from 0 to 10. On this same scale the index 0 corresponds to absence of pain, index 1 to 3 to mild pain, and index 10 to the maximum pain imaginable.

Compound of General Formula (I)

Preferably, the compound of general formula (I) defined above is represented by one of the following formulae (II), (III) and (IV):

(II)
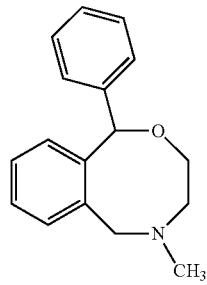

(III)
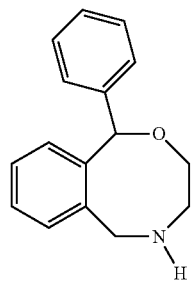

(IV)
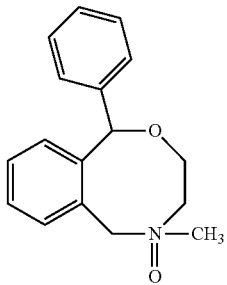

Formula (II) represents nefopam, and formulae (III) and (IV) represent respectively two metabolites of nefopam, namely desmethyl-nefopam and nefopam N-oxide.

Particularly preferably, the compound of general formula (I) as defined above is represented by formula (II) above and corresponds to nefopam.

As understood here, general formula (I) defined above also represents the stereoisomers and mixtures of stereoisomers, notably the racemic mixture, of the compounds of formula (I).

The pharmaceutically acceptable salts of the compounds of general formula (I) defined above will be evident to a person skilled in the art. In particular, the hydrochloride salts of the compounds of general formula (I) as defined above are preferred.

Nefopam hydrochloride is the compound of general formula (I) as defined above that is the most preferred for application of the invention.

COX-2-Selective Inhibitor

As understood here, a COX-2-selective inhibitor is such that it inhibits COX-2 more than COX-1, the inhibition of COX-2 and of COX-1 being measured in the same conditions. It is considered in particular that an inhibitor is selective for COX-2 when the selectivity index of the inhibitor, i.e. the $IC50_{cox-2}/IC50_{cox-1}$ ratio of the inhibitor, in particular measured in whole blood, is less than 1, preferably less than 0.5 and more preferably less than 0.2. The expression "$IC50_{cox}$", well known by a person skilled in the art, denotes the concentration of inhibitor providing 50% inhibition of the maximum activity of the COX in question.

Preferably, the IC50 of the COX-2-selective inhibitors according to the invention with respect to COX-2, in particular measured in whole blood, is less than 5 µM, preferably less than 2 µM and more preferably less than 1 µM.

The inhibition of COX-1 and COX-2, notably in whole blood, can easily be determined by a person skilled in the art. In particular, the inhibition of COX-1 and COX-2 in whole blood can be determined as described by Cryer and Feldman (1998) *Am. J. Med.* 104:413-421, notably pages 414 and 415, paragraphs COX-1 whole blood assay and COX-2 whole blood assay.

Also preferably, the COX-2-selective inhibitor according to the invention belongs to the drug (or therapeutic) class of the COXIBs.

Preferably, the COX-2-selective inhibitor according to the invention is represented by the following general formula (V):

(V)
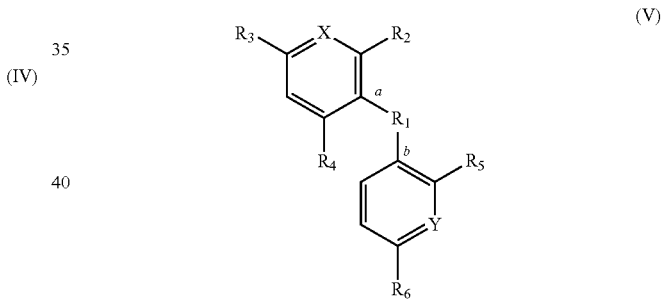

in which:

$R_1$ is selected from the group consisting of NH,

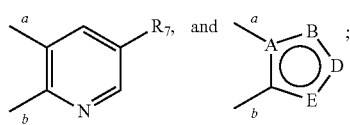

a and b make it possible to determine the orientation of $R_1$;
$R_2$ represents H or a halogen, preferably I, Br, Cl or F, and more preferably Cl;
$R_3$ represents H or $-SO_2R_8$, where $R_8$ represents $-CH_3$, $-NH_2$ or $-NH-CO-CH_2-CH_3$;
$R_4$ represents H or a halogen, preferably I, Br, Cl or F, and more preferably F;
$R_5$ represents H or $CH_2-COOH$;
$R_6$ represents H or $CH_3$;
$R_7$ represents H or a halogen, preferably I, Br, Cl or F, and more preferably Cl;

X and Y represent independently N or CH;

A represents N or C;

B represents N, $CH_2$ or C—$CH_3$;

D represents O, or C—$CF_3$;

E represents N, CH or C=O.

More preferably, the COX-2-selective inhibitor according to the invention is represented by the above-defined general formula (V), provided it is different from diclofenac.

Even more preferably, the COX-2-selective inhibitor according to the invention is represented by the above-defined general formula (V), wherein $R_1$ is selected from the group consisting of:

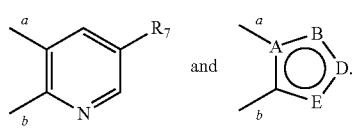

Particularly preferably, the COX-2-selective inhibitor according to the invention is selected from the group consisting of celecoxib, parecoxib, valdecoxib, rofecoxib, etoricoxib, and lumiracoxib; more preferably, the COX-2-selective inhibitor is selected from the group consisting of celecoxib, parecoxib, valdecoxib, rofecoxib, and etoricoxib; and even more preferably the COX-2-selective inhibitor according to the invention is celecoxib.

The formulae of the preferred COX-2-selective inhibitors according to the invention are shown below:

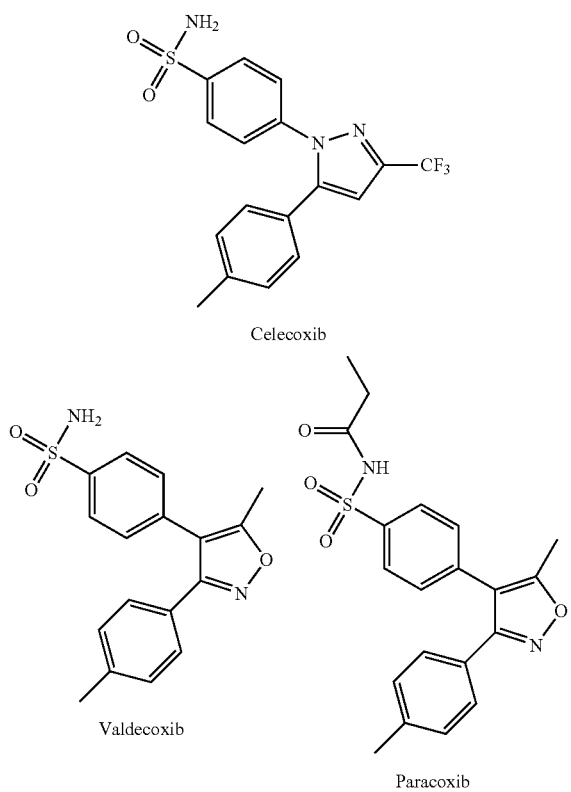

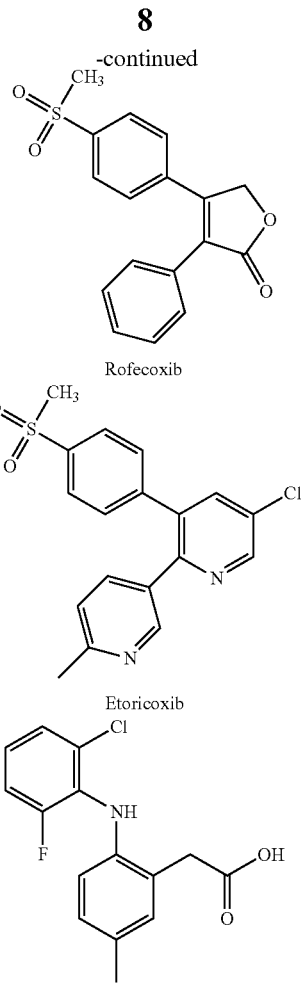

Administration

As understood here, the expression "in combination" or "combination product" means that the compound of general formula (I) as defined above, or a pharmaceutically acceptable salt thereof, and the COX-2-selective inhibitor as defined above, or a pharmaceutically acceptable salt thereof, can be combined within one and the same pharmaceutical composition, and can therefore be administered together, or else can be administered separately, i.e. according to different routes of administration and/or different regimens of administration, provided that when they are administered separately the respective periods of analgesic activity of the compound of general formula (I) and of the COX-2-selective inhibitor overlap wholly or partly, notably so that the compounds can cooperate to exert a synergistic analgesic effect.

Thus, when the compounds are administered separately, the compound of general formula (I) as defined above, or its pharmaceutically acceptable salt, will preferably be administered within 24 hours, more preferably within 2 hours, and even more preferably within one hour, following administration of the COX-2-selective inhibitor as defined above, or of its pharmaceutically acceptable salt, and its administration will optionally be continued for some days thereafter. Conversely, the COX-2-selective inhibitor as defined above, or its pharmaceutically acceptable salt, will preferably be administered within 24 hours, more preferably within 2 hours, and even more preferably within one hour, following administration of the compound of general formula (I) as defined above, or of its pharmaceutically acceptable salt, and its administration will optionally be continued for some days thereafter. In another preferred embodiment of the invention, the compounds according to the invention are administered essentially simultaneously when they are administered separately.

Preferably, the compound of general formula (I) as defined above, or its pharmaceutically acceptable salt, is administered or is in a form suitable for administration by the oral, intravenous or intramuscular route.

Preferably, the COX-2-selective inhibitor as defined above, or its pharmaceutically acceptable salt, is administered or is in a form suitable for administration by the oral route, by injection or locally.

Preferably, when the compound of general formula (I) as defined above, or its pharmaceutically acceptable salt, and the specific inhibitor of COX-2 as defined above, or its pharmaceutically acceptable salt, are combined within one and the same pharmaceutical composition, the latter is administered or is in a form suitable for administration by the oral route, by injection or locally.

Preferably, the compound of formula (I) as defined above, or its pharmaceutically acceptable salt, notably nefopam hydrochloride, is contained in the pharmaceutical compositions or the products defined above, or is administered, at a unit dose from 1 mg to 120 mg, more preferably at a unit dose of 20 mg.

Preferably, the COX-2-selective inhibitor, or its pharmaceutically acceptable salt, notably celecoxib, is contained in the pharmaceutical compositions or the products defined above, or is administered, at a unit dose from 10 mg to 1000 mg, more preferably at a unit dose from 50 mg to 500 mg.

Additional Analgesic Compound

Any analgesic compound may be suitable as additional analgesic compound according to the invention, but it is preferred if it is:
- a morphine compound, such as morphine, fentanyl, remifentanil, alfentanil, sufentanil, nalbuphine, pentazocine, codeine, hydrocodeine, dihydrocodeine, dextropropoxyphene, tramadol, buprenorphine, hydromorphone, oxycodone, or pethidine;
- a non-steroidal anti-inflammatory (NSAID), such as ketoprofen, acetylsalicylic acid, mefenamic acid, fenoprofen, aceclofenac, tiaprofenic acid, alminoprofen, diclofenac, etodolac, flurbiprofen, nabumetone, naproxen, meloxicam, piroxicam, tenoxicam, indometacin, sulindac, floctafenine, phenylbutazone, or nimesulide;
- paracetamol, ziconotide, or caffeine.

Compound of General Formula (VI)

The compound of general formula (VI) defined above is preferably represented by the following formula (VII):

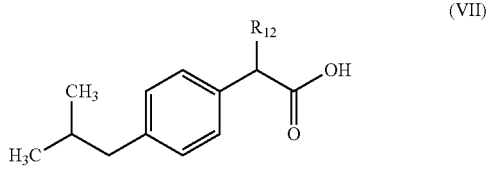

(VII)

in which $R_{12}$ is as defined above.

Also preferably, the compound of general formula (VI) defined above is represented by the following formulae (VIII), (IX) and (X):

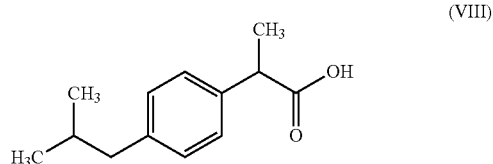

(VIII)

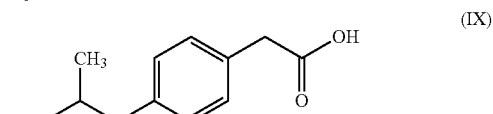

(IX)

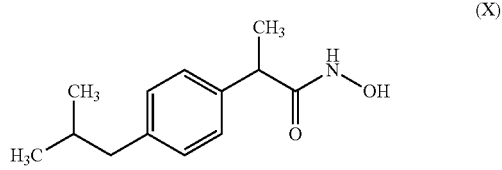

(X)

The above formulae (VIII), (IX) and (X) represent respectively ibuprofen, ibufenac and ibuproxam.

More preferably, the compound of general formula (VI) defined above is represented by the above formula (VIII) and particularly preferably by the following formula (XI):

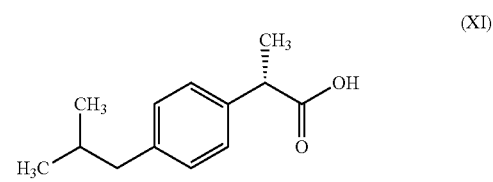

(XI)

Formula (XI) represents the S form of ibuprofen which has the main analgesic properties of ibuprofen.

As understood here, formulae (VI), (VII), (VIII) and (X) defined above also represent stereoisomers and mixtures of stereoisomers, notably the racemic mixture, of the compounds of formulae (VI), (VII), (VIII) and (X).

The pharmaceutically acceptable salts of the compounds of general formula (VI) defined above will be evident to a person skilled in the art. In particular, the salts of lysine, notably of L-lysine, of the compounds of general formula (V) as defined above are preferred, such as the lysine salt of ibuprofen or the monohydrate salt of L-lysine of the S form of ibuprofen.

Moreover, as will be evident to a person skilled in the art, it is easy to synthesize prodrugs of the compounds of formulae (VII), (VIII) and (IX) defined above, i.e. compounds that are quickly transformed in vivo to give the compound of formulae (VII), (VIII) and (IX) defined above, for example by hydrolysis in the blood. Also, apart from the prodrugs of the compounds of formulae (VII), (VIII) and (IX) defined above that are represented by the compounds of formula (VI) for which $R_{13}$ is different from OH, such as ibuproxam, the aim here is preferably to exclude the application of all of the prodrugs of the compounds of formula (VI) defined above.

EXAMPLE

The analgesic effect of a nefopam-celecoxib combination was investigated in the model of abdominal cramps induced in the mouse by intraperitoneal administration of acetic acid. This model of pain induced by a chemical substance corresponds to inflammatory, visceral and acute pain.

A. Material and Methods

1. Animals

Male CD1 mice (bred: C. River) weighing between 25 and 30 grams are used after an acclimatization for at least 7 days in the animal house (temp.=22±2; humidity=50±20%; food SAFE "A04"; nyctohemeral cycle: 12 h/12 h (light: 7 h/19 h–darkness: 19 h/7 h)).

2. Protocol

On the day of the experiment, the non-fasting mice are weighed, marked and distributed at random in batches of 10. The acetic acid solution (Sigma) is prepared at 0.6%, or 60 mg of acetic acid in 10 ml of 0.9% NaCl.

At t=0, the mouse receives celecoxib by the oral route. At t=30 min, the mouse is administered nefopam or its liquid vehicle by the subcutaneous route. At t=60 min, the acetic acid is injected intraperitoneally (0.1 ml/10 g).

The number of abdominal cramps is counted from 5 to 20 minutes after injection of acetic acid. Frank abdominal cramps characterized by stretching of the hindpaws and/or hollowing of the flanks with twisting are regarded as positive.

3. Products

Nefopam hydrochloride (Biocodex, batch 38) (called simply nefopam hereunder) is dissolved in distilled water or 0.9% NaCl. Celecoxib (Celebrex® capsules) is suspended in Tween 80 at 1%.

4. Statistical Analysis

The test used is an analysis of variance for 3 or more groups and a Student t-test for 2 groups. Then the treated group or groups that differ from the control group are determined. The effective doses at 50% of antinociceptive effect (ED50) are calculated using the PharmToolsPro software (version 1.1.27, McCary Group Inc.) according to the method of Tallarida (2000) *Drugs synergism and dose-effect data analysis* CRC Press). At least 10 mice are used for each dose, and at least 3 doses are used for determining the dose-response curve. The dose that produces 50% of antinociceptive effect (50% decrease in number of cramps) is calculated by a standard linear regression analysis of the dose-response curve.

The interaction is evaluated by an isobolographic analysis of the co-administration of a combination of doses at fixed ratio according to Tallarida (2000) op. cit., Tallarida et al. (1989) *Life Sci.* 45:947-961 and Tallarida et al. (1997) *Life Sci.* 61:PL417-PL425. The isobologram is constructed by joining the ED50 of celecoxib with that of nefopam to obtain the line of additivity. The ED50 of the combination is determined by linear regression analysis of the dose-response curve, and it is compared by a t-test with a theoretical additive ED50 obtained using the PharmToolsPro software.

B. Results

1. Nefopam Alone

The subcutaneous administration of nefopam leads to dose-dependent inhibition of the number of cramps induced by acetic acid in the mouse (Table 1). The measured ED50 of nefopam is 2.395±0.215 mg/kg.

2. Celecoxib Alone

Orally administered celecoxib produces a dose-dependent decrease in the number of cramps induced by acetic acid in the mouse, with an ED50 of 40.172±8.060 mg/kg (Table 1). This result is similar to that obtained by Lu et al. (2005) *Acta Pharmacol. Sin.* 26:1505-1511 in the same model (94 mg/kg).

TABLE 1

Specific effects of nefopam and of celecoxib administered alone

| Products (mg/kg) | n | Number of cramps (mean ± SEM) | % variation | ANOVA |
|---|---|---|---|---|
| Nefopam | | | | |
| 0 | 18 | 37.1 ± 2.8 | | |
| 0.3 | 9 | 33.6 ± 3.8 | −9 | ns |
| 1.0 | 10 | 28.0 ± 6.3 | −25 | ns |
| 3.0 | 18 | 16.7 ± 2.0 | −55 | $p < 0.05$ |
| 10.0 | 10 | 7.1 ± 1.7 | −81 | $p < 0.05$ |
| 20.0 | 10 | 0.6 ± 0.3 | −98 | $p < 0.05$ |
| ED50 (mg/kg) = 2.395 ± 0.215 | | | | |
| Celecoxib | | | | |
| 0 | 18 | 31.0 ± 2.9 | | |
| 10 | 10 | 28.2 ± 2.9 | −9 | ns |
| 20 | 10 | 18.1 ± 3.2 | −42 | ns |
| 50 | 10 | 18.9 ± 2.2 | −39 | ns |
| 75 | 10 | 8.6 ± 2.1 | −72 | $p < 0.05$ |
| 150 | 10 | 3.2 ± 1.0 | −90 | $p < 0.05$ |
| ED50 (mg/kg) = 40.172 ± 8.060 | | | | |

($p < 0.05$: ANOVA statistical test followed by Bonferroni or Dunn)

3. Nefopam-Celecoxib Association

Firstly, using the PharmToolsPro software, the fixed proportion of each product for an efficacy level of 50% and the theoretical ED50 that is located on the additivity straight line are determined according to Tallarida (2000) op. cit. This gives a proportion of 0.056 for nefopam and of 0.944 for celecoxib and a theoretical ED50 of 21.330±4.041 mg/kg.

Secondly, compositions having a proportion of 5.6% of nefopam and 94.4% of celecoxib are investigated in the animal model in order to obtain an experimental ED50, which will be compared with the theoretical ED50 of the additivity straight line. Table 2 shows the experimental results obtained. The experimental ED50 is 9.193±0.542 mg/kg (corresponding to 0.515±0.030 mg/kg of nefopam and 8.678±0.512 mg/kg of celecoxib).

Lastly, the experimental ED50 is placed on the isobologram obtained from the data in Table 1 (FIG. 1). It can be seen that the experimental ED50 of the nefopam-celecoxib association is below the additivity straight line, where the theoretical ED50 corresponding to simple additivity is located. The interaction between nefopam and ibuprofen is therefore located in the zone of super-additivity indicating a synergistic relation between the two compounds. Moreover, statistical analysis (Student t-test) gives at $t_{experimental}$ of 4.236 which is greater than the $t_{theoretical}$ of 2.329, consequently the difference between the experimental ED50 and the theoretical ED50 is significant.

TABLE 2

Effect of co-administration of nefopam and celecoxib

| Nefopam (mg/kg) | Celecoxib (mg/kg) | n | Number of cramps (mean ± SEM) | % variation | ANOVA |
|---|---|---|---|---|---|
| 0 | 0 | 12 | 30.2 ± 2.8 | | |
| 0.075 | 1.25 | 10 | 26.8 ± 5.4 | −11 | ns |
| 0.15 | 2.5 | 10 | 24.2 ± 2.9 | −20 | ns |
| 0.30 | 5 | 10 | 19.2 ± 2.4 | −36 | $p < 0.05$ |
| 0.60 | 10 | 9 | 13.1 ± 2.6 | −57 | $p < 0.05$ |
| 1.20 | 20 | 12 | 9.1 ± 2.3 | −70 | $p < 0.05$ |
| 2.40 | 40 | 12 | 5.2 ± 1.1 | −83 | $p < 0.05$ |
| 4.80 | 80 | 12 | 1.8 ± 0.6 | −94 | $p < 0.05$ |
| ED50 (mg/kg) = 9.193 ± 0.542 | | | | | |

($p < 0.05$: ANOVA statistical test followed by Bonferroni or Dunn)

The invention claimed is:

1. A pharmaceutical composition comprising as active substances a therapeutically effective amount of:
   a) nefopam hydrochloride or a pharmaceutically acceptable salt of this compound; and
   b) celecoxib or etoricoxib, or a pharmaceutically acceptable salt thereof;
   wherein the nefopam hydrochloride and celecoxib or etoricoxib, or pharmaceutically acceptable salts thereof, exert a synergistic analgesic effect.

2. The pharmaceutical composition of claim 1, comprising a unit dose from 1 mg to 120 mg of nefopam hydrochloride or of a pharmaceutically acceptable salt thereof.

3. The pharmaceutical composition of claim 1, comprising a unit dose from 10 mg to 1000 mg of celecoxib or etoricoxib or of a pharmaceutically acceptable salt thereof.

4. The pharmaceutical composition of claim 1, wherein the composition is suitable for administration by the oral route, by injection or locally.

5. A method for inducing analgesia or for treating pain in an individual in need thereof, comprising administering to said individual a therapeutically effective amount of the pharmaceutical composition according to claim 1.

6. The method of claim 5, wherein the nefopam hydrochloride in the composition, or a pharmaceutically acceptable salt thereof, is administered at a unit dose of from 1 mg to 120 mg.

7. The method of claim 5, wherein the celecoxib or etoricoxib, or a pharmaceutically acceptable salt thereof, is administered at a unit dose of from 10 mg to 1000 mg.

8. The method of claim 5, wherein the composition, or a pharmaceutically acceptable salt thereof, is administered by the intravenous, oral, or intramuscular route.

9. The method of claim 5, wherein the celecoxib or etoricoxib of the composition, or pharmaceutically acceptable salts thereof, is administered orally, by injection or locally.

* * * * *